United States Patent [19]

Neigel

[11] Patent Number: 4,642,390

[45] Date of Patent: Feb. 10, 1987

[54] PROCESS FOR THE MANUFACTURE OF ACETALS OF CHLOROACETALDEHYDE

[75] Inventor: Dennis Neigel, Whitehouse Station, N.J.

[73] Assignee: National Starch and Chemical Corporation, Bridgewater, N.J.

[21] Appl. No.: 868,457

[22] Filed: May 30, 1986

[51] Int. Cl.$^4$ .................. C07C 41/48; C07C 41/50; C07C 41/58

[52] U.S. Cl. .................. 568/604; 568/596; 568/591; 549/455; 560/266

[58] Field of Search .............. 568/604, 596, 591; 549/455; 560/266

[56] References Cited

U.S. PATENT DOCUMENTS

| | | | |
|---|---|---|---|
| 2,330,570 | 9/1943 | Filachione | 260/615 |
| 2,411,826 | 11/1946 | Filachione | 260/615 |
| 2,803,668 | 8/1957 | Morris et al. | 260/615 |
| 4,130,592 | 12/1978 | Vogt et al. | 568/604 |
| 4,440,959 | 4/1984 | Deinhammer | 568/604 |

OTHER PUBLICATIONS

Filachione, E. M., Am. Chem. Soc., vol. 61, 1939, pp. 1705–1706.

Primary Examiner—Howard T. Mars
Attorney, Agent, or Firm—Edwin M. Szala; Ellen T. Dec

[57] ABSTRACT

A semi-continuous process for the manufacture of acetals of chloroacetaldehyde is described. In a preferred embodiment of the invention, chloroacetaldehyde dimethyl acetal is prepared by introducing chlorine and vinyl acetate through separate inlets into the upper opening of a cooled vertical packed column to form an intermediate product. The intermediate flows through the column, and optionally a static mixer, into a cooled batch reactor precharged with an excess of methanol to form the crude acetal product. Isolation and purification of the product is accomplished by known batch-type procedures.

8 Claims, 1 Drawing Figure

PROCESS FOR THE MANUFACTURE OF ACETALS OF CHLOROACETALDEHYDE

BACKGROUND OF THE INVENTION

This invention relates to a new process for the manufacture of acetals of alpha-halogenated aldehydes. more particularly, it relates to an improved process for the manufacture of chloroacetaldehyde dimethyl acetal.

A number of processes for the manufacture of chloroacetaldehyde acetals are known and have been disclosed in the prior art. For example, Ullman, Enzyklopadie der technischen Chemie, 4th edition 1975, vol. 9 page 375, describes the manufacture of chloroacetaldehyde acetals by chlorinating vinyl compounds in alcoholic medium. U.S. Pat. Nos. 2,803,668 and also 4,130,592 teach the chlorination of vinyl chloride which produces considerable amounts of 1,1,-2-trichloroethane as a byproduct. Because of its similar boiling point, it is difficult to separate the by-product from the desired chloroacetaldehyde dimethyl acetal. Moreover, a particular disadvantage of these methods relate to the highly toxic nature of the vinyl chloride starting material.

The reaction of vinyl acetate and a halogen in the presence of excess alcohol has been known for many years: see U.S. Pat. Nos. 2,330,570 and 2,411,826 and J. Am. Chem. Soc., vol. 61 (1939) pages 1705–1706 by E. M. Filachione. The acetals were isolated from the reaction mixture by customary methods, e.g., by the addition of water and by subsequent extraction of the acetal layer with a water-immiscible solvent such as ether, chloroform or benzene. The organic extract was washed with water and/or an aqueous alkaline solution, such as sodium bicarbonate solution, in order to remove acid or other water-soluble by-products, after which the organic solvent was then distilled off and the acetal purified by distillation. Because of relatively poor yields (approximately 46 to 53%) and also that large amounts of solvent have to be distilled, the process is inappropriate for the manufacture of chloroacetaldehyde dimethyl acetal on an industrial scale.

U.S. Pat. No. 4,440,959 issued Apr. 3, 1984 to Wacker-Chemie GmbH relates to an improved process for the manufacture of chloroacetaldehyde dimethyl acetal by reacting vinyl acetate and chlorine in a methanolic solution at a temperature of less than 20° C. When the addition of chlorine is completed, low boiling constituents are partially or completely distilled off from the reaction mixture. The liquid residue is neutralized with solid oxides or carbonates of calcium and magnesium while maintaining a temperature of from 20° to 60° C. until the aqueous extract has a pH of greater than 5. When neutralization is completed, the reaction mixture forms two liquid phases and the upper organic layer containing the desired product is separated and fractionally distilled. The patent states that pure chloroacetaldehyde dimethyl acetal is obtained as the main fraction with yields of more than 90% calculated on the amount of vinyl acetate.

The process described in U.S. Pat. No. 4,440,959 is a batch-type operation, and none of the prior art applicant is aware of relating to the production of such compounds teaches or suggests the use of a continuous or semi-continuous process.

Particularly where large scale industrial operations are contemplated, there is a need for a safe and economical, continuous process for the manufacture of acetals of alpha-halogenated aldehydes. The acetals described herein are useful as intermediates in the production of other compounds which have commercial uses.

SUMMARY OF THE INVENTION

In accordance with the process of the present invention, acetals of alpha-halogenated aldehydes are manufactured by a semi-continuous process in which elemental chlorine or bromine is introduced and brought into reaction with vinyl acetate in a cooled, vertical packed column or a Graham condenser which is particularly useful in place of the packed column for small scale systems. The use of the term semi-continuous herein is intended to mean a continuous process with respect to the formation of the crude acetal product and a batch-type process with respect to the isolation of the acetal from the reaction product mixture and its subsequent purification.

It is noted that the semi-continuous process herein is equally feasible with either chlorine or bromine, although the higher price of the latter halogen encourages use of chlorine. For convenience in the remainder of the specification and claims, where reference is made to chlorine, it is intended to mean either chlorine or bromine.

The reaction of chlorine with the vinyl acetate is run as a continuous reaction process. The chlorine and vinyl acetate are fed through separate inlets (ports) of a "Y" adapter at the top of the column in stoichiometric amounts with respect to the chlorine and vinyl acetate and enter into an exothermic reaction. The intermediate product formed within the column flows down by gravity into a static mixer which provides a thorough mixing of any unreacted starting materials and assures a complete reaction of chlorine and vinyl acetate. While the static mixer is not essential to the process and optionally may be omitted at the practitioner's discretion, reaction efficiency may be diminished. Thereafter, the intermediate (1,2-dichloroethyl acetate) flows into a cooled "batch reactor" containing a three to five-fold molar excess of a lower alcohol where further reaction of the intermediate with the alcohol takes place to provide the crude acetal.

The batch reactor is equipped with a reflux condenser (which itself is vented with a line directed to a caustic scrubber) so the low boiling vapors formed in the batch reactor are returned to the reactor. The batch reactor is ordinarily cooled with jacketed cold water (having a temperature of about 17°–20° C.).

When the crude acetal is collected inthe reactor in an amount convenient for further working, the feed of starting materials is stopped and the reaction is terminated. As will be made clear in the description of the invention that follows, the work-up of the crude acetal to yield the purified product is accomplished by known, batch-type procedures.

By utilizing this semi-continuous process, a number of benefits are realized over batch-type processes of the prior art. Thus, the process of forming the 1,2-dichloroethyl acetate intermediate in the absence of the alcohol eliminates the possibility of two prominent side reactions, the addition of the alcohol or hydrogen chloride across the vinyl double bond. The net effect is improved yield. Previous batch operations necessitated reaction temperatures of <20° C. to avoid formation of these side reaction products. With this continuous process, higher reaction temperatures can be used without byproduct formation. Improved safety is obtained since relatively small amounts of reactant chemicals are under process at the reaction site at any given time as compared to batch-type operations. Improved process control is obtained since the continuous system has a number of operating parameters which can be adjusted to maximize conversion and operation efficiency.

DESCRIPTION OF THE PREFERRED EMBODIMENTS

Figure 1:
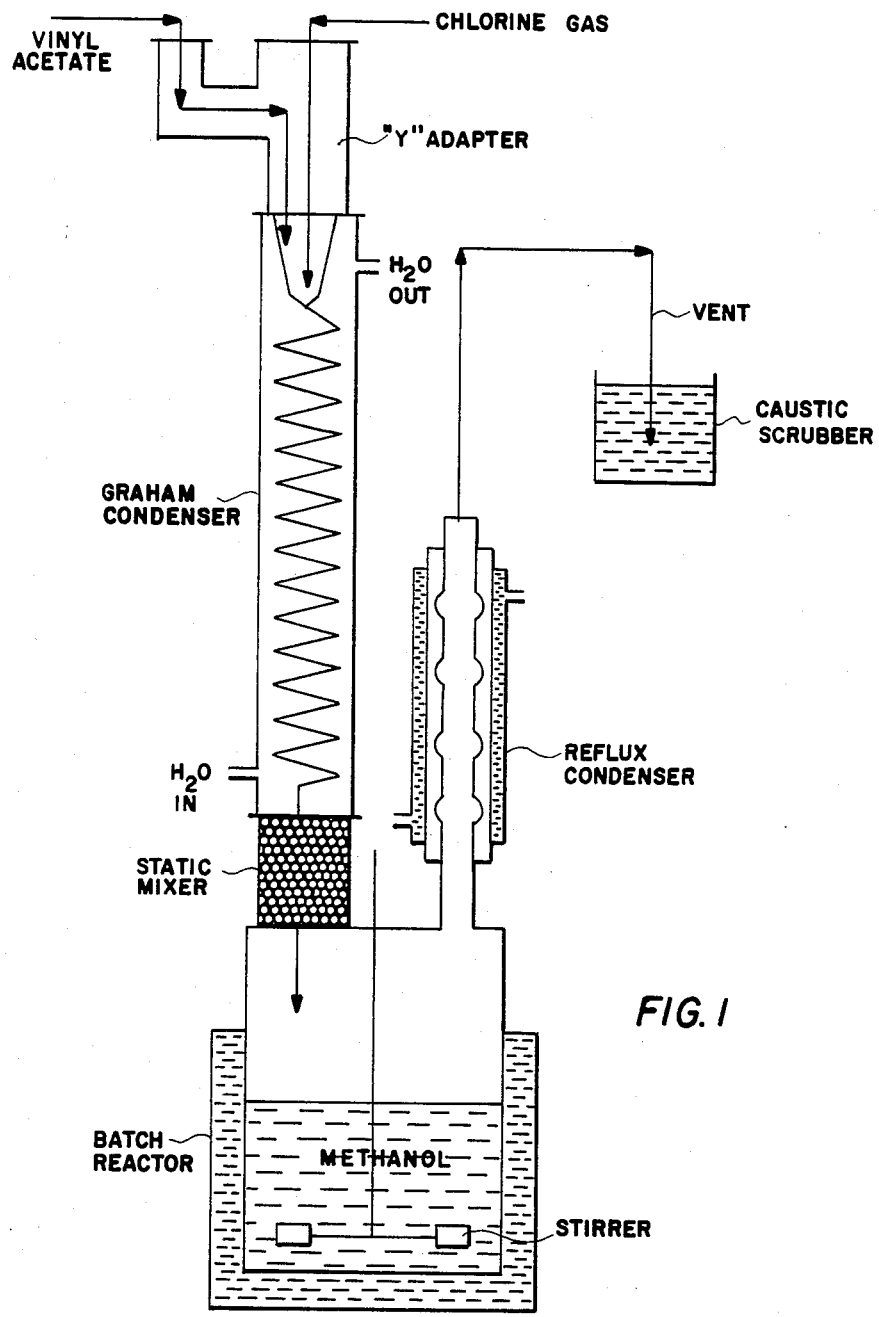

With respect to apparatus, accompanying FIG. 1 schematically shows a suitably fitted column (Graham condenser) arranged to carry out the process of the present invention. Thus, the condenser is fitted at its upper end with a "Y" adapter to permit the continuous addition of chlorine gas in one port and the addition of vinyl acetate in the other port. A cooled, vertical packed column may also be used and the packing, preferably, is of the ceramic saddle type, although glass beads, plastic honeycomb and other common, corrosion resistant packing materials can also be used. The packed column (or condenser) as well as the other equipment used in the process will ordinarily be made of glass (or glass lined) or be made of other material able to withstand the corrosive properties of the chemicals used and formed in the present process. The lower opening of the condenser is fitted with a static mixer, preferably containing glass beads, and a jacketed "batch reactor" which is adapted to receive the intermediate product. The batch reactor is fitted with a reflux condenser having the upper opening vented to permit residual vapors to escape into a caustic scrubber. When the process is started, the batch reactor will be charged with an excess of a lower alcohol suitable for reacting with the intermediate formed from chlorine and vinyl acetate. While FIG. 1 schematically shows apparatus useful in carrying out the process herein, the invention is not limited to the illustrated apparatus. Significant variations or modifications in the apparatus will not necessarily change or destory the semi-continuous process of the invention.

It is an advantage of the present process that it can be utilized to prepare a variety of acetals, e.g., dialkyl acetals where the alkyl portion of the acetal may be methyl, ethyl, propyl or isopropyl, and dialkylene, cyclic and dicyclic acetals. To prepare a selected acetal it is only necessary to provide the appropriate lower alchol ($C_1$-$C_6$) in the batch reactor. Useful alcohols include methanol, ethanol, isopropanol, n-propanol, 2-butanol, ethylene glycol, cyclohexanol, 2-amyl alcohol, allyl alcohol and methallyl alcohol. Use of mixed alcohols will provide mixed acetals, and use of ethylene glycol will provide the corresponding cyclic and polymeric acetals.

In the manufacture of chloroacetaldehyde dimethyl acetal in accordance with the process of this invention, a flow of chlorine gas is brought in contact with a feed of vinyl acetate. Conveniently, the two feed components are introduced through separate inlets of a "Y" adapter into a reaction site of a vertical packed column where the components enter into a exothermic reaction. Further mixing and reaction of the starting materials takes place as the reactants flow downward by gravity in the cooled column or condenser. Ordinarily, the chlorine and vinyl acetate are fed in stoichiometric amounts at constant rates measured in moles/minute so that one mole of chlorine is available to react with one mole of vinyl acetate.

The rate of feeding the column is mainly governed by the size of the column in which the process is run. For example, the inner diameter of the packed column (or Graham condenser) as well as the length will be strong factors in determining the parameter of feeding the starting chemicals to the reaction site. As a useful quideline, when the process is run in columns having an inner diameter of 50 mm with a height of about 110-120 cm, the chlorine and vinyl acetate reactants can be fed at a rate of about 0.14 to 0.30 moles/minute. Practitioners will be able to adjust the feed to suitable rates with no difficulty. The column (or condenser) is cooled as necessary to maintain the intermediate at the point of exit from the column at a temperature of 25°-50° C. and preferably at about 35°-40° C. While the reaction may be run at temperatures which are several degrees above 40° C., there is an accompanying loss of yield. Temperatures below 35° C. are permissible but require stronger cooling or a slower feed rate of starting materials.

As the intermediate is formed in the column, it flows into the static mixer in an effect to eliminate or minimize any unreacted starting materials, and thereafter flows into a reservoir of methanol. Prior to starting the process, the batch reactor is charged with methanol in a three to five fold molar excess as compared to a mole of the 1,2-dichloroethyl acetate intermediate that will be produced. The intermediate reacts with the methanol stoichiometrically to provide the crude acetal in the batch reactor. Stirring of the methanol is started prior to the addition of the intermediate and, preferably, continued for 10 to 20 minutes after all of the intermediate has been added.

The acetal may be recovered from the crude acetal reaction mixture by any of several convenient, known procedures. Thus, in one such procedure, calcium oxide or calcium hydroxide is added to the mixture to provide a pH greater than 3, preferably 3.1-3.4, and to produce two phases: an upper organic layer and a lower aqueous layer. The upper layer containing the product can now be purified either by fractional distillation or by the addition of 20-30% aqueous sodium hydroxide and subsequent phase separation of chloroacetaldehyde dimethyl acetal from the hydrolyzed methyl acetate to yield high purity product.

The following examples illustrate the process of this invention although it will be understood that these examples are included for purposes of illustration and are not intended to limit the scope of the invention.

EXAMPLE 1

Apparatus similar to that illustrated in FIG. 1 was assembled to provide the means of running the semi-continuous process for the manufacture of chloroacetaldehyde dimethyl acetal.

Thus, a "Y" adapter was fitted into the upper opening of a 50 cm vertically positioned Graham condenser providing inlets for the feed of chlorine and vinyl acetate starting materials. The bottom opening of the condenser was fitted into a static mixing chamber (2.5 cm in diameter and 10 cm in height) filled with glass beads. The lower opening of the mixing chamber was fitted into a 12-liter Morton flask batch reactor cooled by jacketed water, and equipped with a paddle stirrer and a reflux condenser which itself was vented to a caustic scrubber.

Dry methanol, 3840 g. (120 moles) was added to the Morton flask and the stirrer was started at 300 rpm. Full cooling (13° C.) was applied to the cooling jackets of both the flask and condensers, and the reactor was started by simultaneously initiating flows of chlorine and vinyl acetate at equimolar rates into the inlets of the "Y" adapter.

The feed streams (chlorine was fed at about 10 g per minute and vinyl acetate was fed at about 12.1 g per minute) were brought together in the lower portion of the adapter and flowed by gravity and slight pressure exerted by the chlorine gas downward through the condenser's spiral tubing to form the 1,2-dichloroethyl acetate intermediate reaction product. The rates of feeding the reactants were controlled to maintain the intermediate at a temperature of about 40° C. at its exit from the condenser. The reaction product (mixture) flowed through the static mixer, where any remaining free chlorine and vinyl acetate were mixed and reacted. The reaction product flowed by gravity from the mixer into the batch reactor which was precharged with methanol. Cooling of the Morton flask jacket was continued in order that the temperature of the mixture did not exceed 40° C.

The continuous reaction is carried on until a total 2130 g (30 moles) of chlorine and 2580 g (30 moles) of vinyl acetate were fed through the condenser. Analysis by gas chromatography of the reaction product in the batch reactor after the reactant feeds were terminated indicated an 84.4% conversion to chloroacetaldehyde dimethyl acetal.

Stirring of the batch reactor was continued for about 15 minutes after which the reaction mixture was neutralized with 1315 g of calcium hydroxide (slow addition) to pH 3.1–3.4 with cooling so that the mixture was maintained from 40°–50° C. Additional cooling was supplied to cool the reaction mixture to room temperature. Stirring was terminated and the neutralized reaction mixture was allowed to phase separate for one hour. The upper organic layer was separated and analyzed by gas chromatography at 65.2% chloroacetaldehyde dimethyl acetal (total layer weight was 4764 g) which calculated to a product yield of 83.2%. The upper organic layer was thereafter fractionally distilled under reduced pressure to yield 3106 g of chloroacetadehyde dimethyl acetal, b.p. 55° C. at 50 mm Hg, of greater than 99% purity measured by gas chromatography. The pure compound has a refractive index of 1.4148±0.0005 at 20° C. and a specific gravity of 1.09–1.10 at 25° C.

EXAMPLE 2

The process of Example 1 was repeated except that 120 moles of ethanol was charged (in place of methanol) in the batch reactor. Analysis by gas chromatography of the upper organic layer from the batch reactor showed a product yield of 78%. Fractional distillation yielded 3568 g of chloroacetaldehyde diethyl acetal, b.p. 54° C. at 16 mm Hg. The pure compound has a refractive index of 1.4171±0.0005 at 20° C.

EXAMPLE 3

The process of Example 1 was repeated except that 120 moles of isopropanol was charged (in place of methanol) in the batch reactor. Analysis by gas chromatography of the upper organic layer from the batch reactor showed a product yield of 43%. Fractional distillation yielded 2328 g of chloroacetaldehyde diisopropyl acetal.

EXAMPLE 4

The process of Example 1 was repeated except that 120 moles of n-propanol was charged (in place of methanol) in the batch reactor. Analysis by gas chromatography of the upper organic layer from the batch reactor showed a product yield of 45%. Fractional distillation yielded 2437 g of chloroacetaldehyde dipropyl acetal.

EXAMPLE 5

The process of Example 1 is repeated using 120 moles of cyclohexanol in place of methanol to yield the corresponding dicyclohexyl acetal of chloroacetaldehyde.

Now that the preferred embodiments of the present invention have been described in detail, various modifications and improvements thereon will become readily apparent to those skilled in the art. Accordingly, the spirit and scope of the invention are to be limited only by the appended claims and not by the foregoing specification.

What is claimed is:

1. A semi-continuous process for the manufacture of chloroacetaldehyde acetals comprising the steps of:
   (a) providing a cooled vertical packed column or Graham condenser fitted at its lower end with a cooled batch reactor charged with a lower alcohol,
   (b) introducing chlorine and vinyl acetate at a constant rate and stoichiometric amounts with respect to chlorine and vinyl acetate at the upper end of the column or condenser.
   (c) cooling the column or condenser to maintain the temperature of the intermediate formed from the chlorine and vinyl acetate at about 25° to 50° C., at the point of exit from the column or condenser,
   (d) directing the flow of intermediate into the batch reactor containing an excess of a lower alcohol to provide the crude acetal product.

2. The process of claim 1 wherein the batch reactor contains a three to five molar excess of a lower alcohol as compared to the total of intermediate to be added thereto.

3. The process of claim 2 wherein the alcohol is selected from the group consisting of methanol, ethanol, isopropanol, n-propanol, ethylene glycol, cyclohexanol, 2-butanol, 2-amyl alcohol, allyl alcohol and methallyl alcohol.

4. The process of claim 1 where a static mixer is employed between the column or condenser and the batch reactor.

5. The process of claim 1 wherein the vertical packed column is a glass column and contains glass beads or ceramic, saddle-type packing.

6. The process of claim 1 wherein the reaction mixture containing the crude acetal product in the batch reactor is neutralized with calcium hydroxide to pH 3.1–3.4, cooled to room temperature, the product layer is separated from the aqueous layer and fractionally distilled under reduced pressure to yield the purified acetal.

7. The process of claim 5 wherein the alcohol is methanol or ethanol.

8. The process of claim 1 wherein the temperature of the intermediate at its point of exit from the column or condenser is maintained at 35°–40° C.

* * * * *